United States Patent
Feltham

(10) Patent No.: US 9,410,626 B2
(45) Date of Patent: Aug. 9, 2016

(54) SENSOR PROBE SEAL

(71) Applicant: Pall Corporation, Port Washington, NY (US)

(72) Inventor: Nigel David Feltham, Chandlers Ford Eastleigh (GB)

(73) Assignee: Pall Corporation, Port Washington, NY (US)

( * ) Notice: Subject to any disclaimer, the term of this patent is extended or adjusted under 35 U.S.C. 154(b) by 394 days.

(21) Appl. No.: 13/949,953

(22) Filed: Jul. 24, 2013

(65) Prior Publication Data

US 2015/0030514 A1    Jan. 29, 2015

(51) Int. Cl.
*B01L 99/00* (2010.01)
*F16J 15/10* (2006.01)
(Continued)

(52) U.S. Cl.
CPC ............... *F16J 15/10* (2013.01); *C12M 23/00* (2013.01); *C12M 23/26* (2013.01); *C12M 23/46* (2013.01); *C12M 37/04* (2013.01); *C12M 41/00* (2013.01)

(58) Field of Classification Search
CPC ......... B01L 3/561; B01L 3/563; B01L 3/565; C12M 23/00; C12M 23/02; C12M 23/14; C12M 23/26; C12M 23/46
USPC .......................................... 422/544, 545, 546
See application file for complete search history.

(56) References Cited

U.S. PATENT DOCUMENTS 8,123,397 B2   2/2012   Baumfalk et al.
8,304,231 B2   11/2012  Röll
(Continued)

FOREIGN PATENT DOCUMENTS

EP   0 424 617 A2    5/1991
JP   H09-042550 A    2/1997
(Continued)

OTHER PUBLICATIONS

Japanese Patent Office, Notice of Reasons for Rejection and Prior Art Search Result, Jun. 23, 2015, 4 pages, Japan.
(Continued)

*Primary Examiner* — Jill Warden
*Assistant Examiner* — Dwayne K Handy
(74) *Attorney, Agent, or Firm* — Leydig, Voit & Mayer, Ltd.

(57) ABSTRACT

A sealing system is provided for preventing leakage of a fluid from a fluid-containing chamber when a sensor probe for measuring fluid conditions within the chamber is inserted into the chamber. The sealing system has at least one port in fluid communication with the fluid-containing chamber. The port has a stem projecting outwardly from the chamber, a tapered flange, and a stem passageway in fluid communication with the chamber interior. A probe seal which is adapted to attach to the stem forms a seal between the port and the sensor probe and prevents fluid in the processing chamber from leaking past the probe seal. The probe seal has spaced-apart inner and outer skirts. The inner skirt forms a seal passageway which is in fluid communication with the chamber, and an inner end disposed to enter the stem passageway when the probe seal is attached to the stem. The inner skirt has a seal member disposed near the inner end for sealably compressing against the probe sensor and the stem passageway to form a leak-tight seal in response to insertion of the sensor probe into the seal passageway. The inner and outer skirt also form a skirt channel adapted to receive the tapered flange of the stem when the inner skirt is inserted into the stem passageway.

12 Claims, 5 Drawing Sheets

(51) Int. Cl.
*C12M 1/34* (2006.01)
*C12M 1/00* (2006.01)
*C12M 3/00* (2006.01)
*C12M 1/12* (2006.01)

(56) References Cited

U.S. PATENT DOCUMENTS

| | | |
|---|---|---|
| 8,859,949 B2 | 10/2014 | Baumfalk et al. |
| 2007/0292940 A1 | 12/2007 | Roll |
| 2010/0089475 A1 | 4/2010 | Tracey |
| 2011/0111489 A1 | 5/2011 | Beese et al. |
| 2011/0233210 A1 | 9/2011 | Fatherazi et al. |
| 2012/0091326 A1 | 4/2012 | Baumfalk et al. |
| 2013/0084030 A1 | 4/2013 | Staheli et al. |

FOREIGN PATENT DOCUMENTS

| | | |
|---|---|---|
| WO | WO 2006/017951 A1 | 2/2006 |
| WO | WO 2010/145747 A1 | 12/2010 |
| WO | WO 2013/052299 A1 | 4/2013 |
| WO | WO 2013/063550 | 5/2013 |

OTHER PUBLICATIONS

Intellectual Property Office of Singapore, Search Report in Singapore Patent Application No. 10201404206P (Oct. 14, 2014).
European Patent Office, Extended European Search Report in European Patent Application No. 14 177 659.1 (Jan. 21, 2015).

SENSOR PROBE SEAL

TECHNICAL FIELD

This invention relates to bio-pharmaceutical containers and, more particularly, sensor probes used to measure the conditions within the containers.

BACKGROUND

In the biotechnology and pharmaceutical industry, sterile liquids must be manufactured, processed, manipulated, transported and stored. Processing includes mixing sterile liquids and/or solids in a controlled manner under sterile conditions. Mixing is a critical operation in drug production and other biopharmaceutical processes, including, for example, buffer and media preparation, cell culture growth, in-process unit operations such as low pH viral inactivation and final formulation. Processing, transport and storage may occur in enclosed processing chambers including, for example, disposable bags, biocontainers and bioreactors.

Many mixing operations require carefully monitoring of on-line parameters such as temperature, pH, conductivity, and the like. Sensor probes are used to measure the conditions in the liquid in the processing chamber. Manifolds on the exterior of the processing chamber typically have ports adapted to receive sensors and permit the sensors to access the interior of the processing chamber. A sensor probe is inserted into and through the ports so that the end of the sensor probe accesses and measures the condition of the processing chamber.

Unfortunately, when the sensor is inserted into the processing chamber, fluid from the processing chamber may leak past the sensor probe and accumulate in the sleeve surrounding the probe. The fluid product which leaks outside the chamber and into the probe sleeve may become unviable and unusable. In extreme cases, fluid which leaks past the sensor probe, may drip out of the probe sleeve during disassembly, creating a messy and other undesirable conditions.

SUMMARY OF THE INVENTION

In one embodiment of the present invention, a biological processing system is provided which incorporates a unique probe seal that forms a fluid-tight seal between the system's fluid port and a sensor probe. The fluid processing chamber, which has an interior for receiving and processing fluids, is adapted to work in conjunction with a sensor assembly which uses a sensor probe to measure conditions in the chamber.

The processing chamber has at least one port disposed on the chamber for receiving the sensor probe and permitting the sensor probe to access the chamber interior. The port comprises a stem projecting outwardly from the chamber. The stem comprises a tapered flange and an interior wall forming a stem passageway disposed between interior and outer openings and in fluid communication with the chamber interior.

The probe seal forms a seal between the port and the sensor probe and prevents fluid in the processing chamber from leaking past the probe seal. The probe seal comprises spaced-apart inner and outer skirts. The inner skirt has a wall forming a seal passageway for receiving the sensor probe and permitting the sensor probe to enter the chamber when the probe seal is attached to the stem. The inner skirt also has a seal member for sealably compressing against the probe sensor and the stem passageway to form a teak-tight seal. The inner and outer skirt form a skirt channel adapted to receive the tapered flange of the stem when the inner skirt is inserted into the stem passageway.

In a preferred embodiment, the stem has an annular flange disposed between the chamber and the tapered flange, so that the annular and tapered flanges form a channel. The probe seal is preferably comprised of a flexible polymeric material adapted to permit the outer skirt to flexibly engage the tapered flange when the tapered flange is inserted into the skirt channel. A cable tie, disposed in the skirt channel, may attach the outer skirt to the stem.

In another preferred embodiment, the seal member is located near the interior end of the inner skirt which is inserted into the stem passageway. The seal member tapers inwardly towards the probe sensor and away from the wall forming the stem passageway. In response to insertion of the probe seal into the seal passageway, the probe seal engages the inwardly projecting seal member and pushes the seal member into sealing contact with the walls of the seal passageway. The seal member is preferably thicker than the inner skirt wall so that when the sensor probe is inserted through the probe seal passageway, the seal member may sealably engage the sensor probe without interference from the wall of the inner skirt.

In yet another embodiment, the inner skirt comprises a neck disposed between the seal member and the inner skirt. The neck is thinner than the seal member so that the seal member may flex outwardly into sealing engagement with stem passageway in response to insertion of the sensor probe into the seal passageway. The seal member is preferably disposed outboard of the outer skirt to facilitate insertion of the inner skirt into the stem passageway.

In another embodiment of the invention, a sealing system is provided for preventing leakage of a fluid from a fluid-containing chamber when a sensor probe for measuring fluid conditions within the chamber is inserted into the chamber. The sealing system comprises at least one port in fluid communication with the fluid-containing chamber. The port comprises a stem projecting outwardly from the chamber. The stem also comprises a tapered flange and an interior wall forming a stem passageway disposed between interior and outer openings and in fluid communication with the chamber interior.

A probe seal is provided for forming a seal between the port and the sensor probe and preventing fluid in the processing chamber from leaking past the probe seal. The probe seal comprises spaced-apart inner and outer skirts. The inner skirt comprises a wall forming a seal passageway wherein the seal passageway is in fluid communication with the chamber. The inner skirt also comprises an interior end disposed to enter the stem passageway when the probe seal is attached to the stem. The inner skirt has a seal member disposed near the interior end for sealably compressing against the sensor probe and the stem passageway to form a leak-tight seal in response to insertion of the sensor probe into the seal passageway. The inner and outer skirt also form a skirt channel adapted to receive the tapered flange of the stem when the inner skirt is inserted into the stem passageway.

In a preferred embodiment, the seal member is thicker than the inner skirt wall on that when the sensor probe is inserted through the probe seal passageway, the seal member may sealably engage the sensor probe without interference from the wall of the inner skirt.

In another embodiment, the system comprises an annular flange disposed so that a channel is defined by the annular and tapered flanges. The probe seal is comprised of a flexible polymeric material adapted to permit the outer skirt to flexibly engage the tapered flange when the tapered flange is inserted into the skirt channel. A cable tie which fits within the channel may releasably attach the outer skirt and stem together.

In yet another embodiment, the seal member is located near the interior end of the inner skirt which is inserted into the stem passageway. The seal member tapers inwardly towards the probe sensor and away from the wall forming the stem passageway to facilitate insertion of the probe seal into the stem passageway. The seal member may also be disposed outboard of the outer skirt to assist insertion of the inner skirt into the stem passageway.

In a preferred embodiment, the inner skirt comprises a neck disposed between the seal member and the inner skirt. The neck is thinner than the seal member so that the neck permits the seal member to flex outwardly into sealing engagement with stem passageway in response to insertion of the probe seal into the seal passageway.

BRIEF DESCRIPTION OF THE DRAWINGS

The preferred embodiments of the present invention are explained in greater with reference to the following drawings. While various illustrative embodiments of the present invention are shown in the following drawings, the drawings should not be used to limit the scope of the present invention.

DETAILED DESCRIPTION OF PREFERRED EMBODIMENTS

It will be appreciated that this detailed description provides exemplary embodiments of the invention. Since other embodiments of the invention may differ in detail from the embodiments in this detailed description, the detailed description is intended to reference the particular embodiments being discussed at that point and is not intended to imply any limitation as to the scope of the invention more generally.

Figure 1:
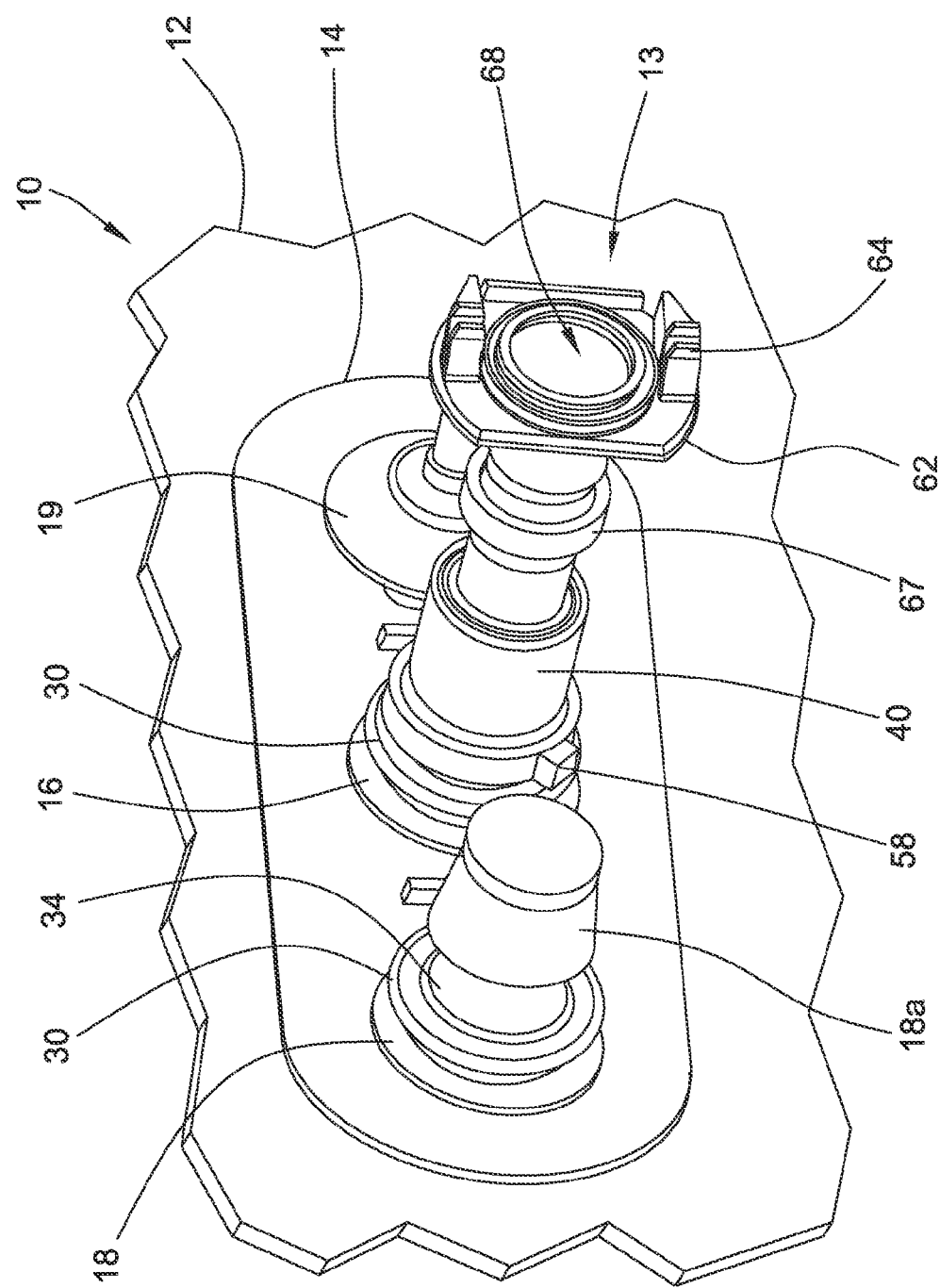
FIG. 1 is a perspective view of a processing chamber having a sensor port manifold, a sensor probe seal and a portion of a sensor probe assembly made in accordance with the present invention.
Figure 2:
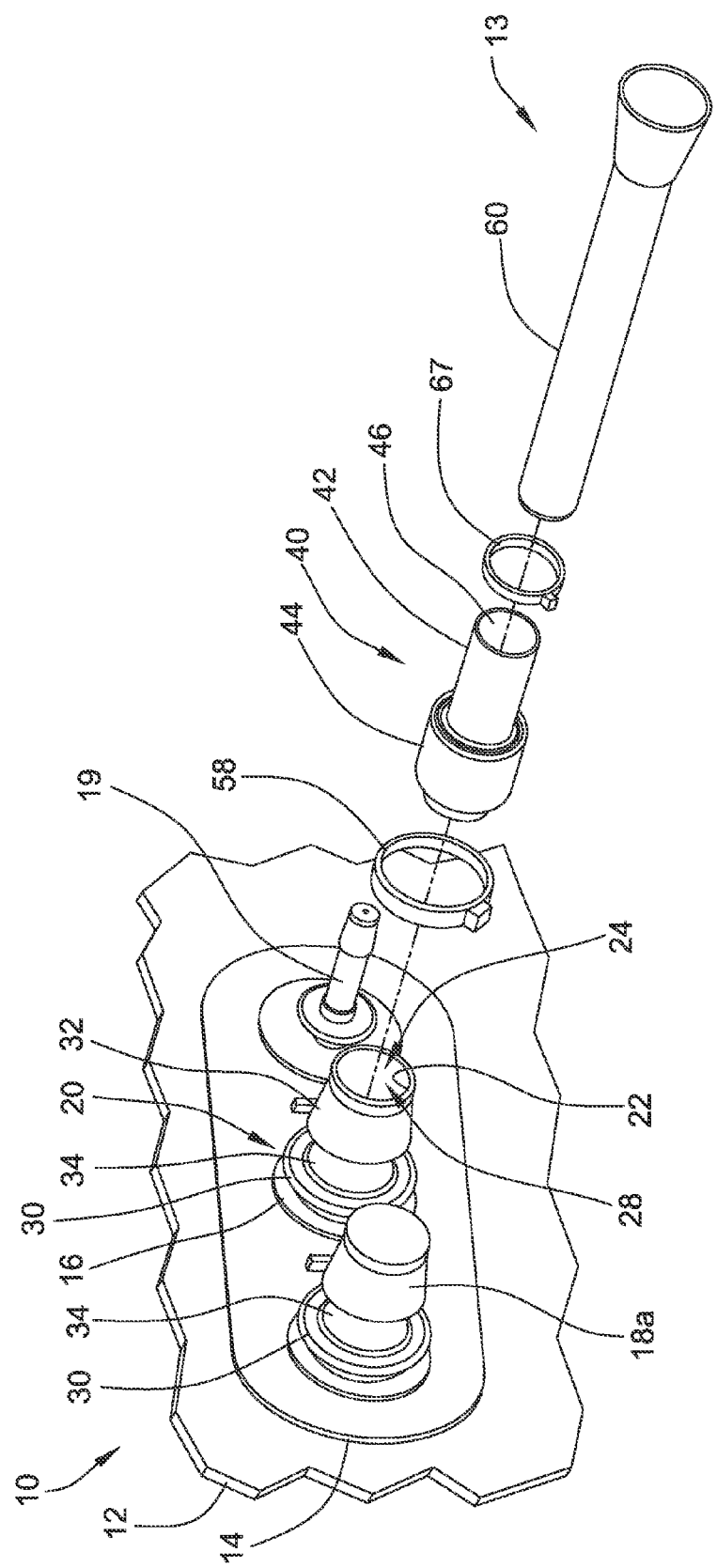
FIG. 2 is an exploded view of a processing chamber having a sensor port manifold, and a sensor probe seal and a portion of a sensor probe assembly made in accordance with the present invention.

FIG. 1 illustrates one embodiment of a processing system 10 incorporating features of the present invention. The illustrated system is a processing chamber 12 which may be used to manufacture, process, manipulate, transport and/or store sterile or non-sterile liquids in the biological, pharmaceutical and other industries. While the invention is described in connection with the processing chamber, it is applicable to seal any port used to access liquids and/or solids in any sort of liquid container. The processing chamber 12 is preferably a processing bag sometimes called a biocontainer or bioreactor which is preferably made of a flexible polymeric material.

The chamber 12 has at least one opening (not shown) to fill and empty the bag. Mixing mechanisms (not shown) may be incorporated in the processing chamber 12.

Figure 3:
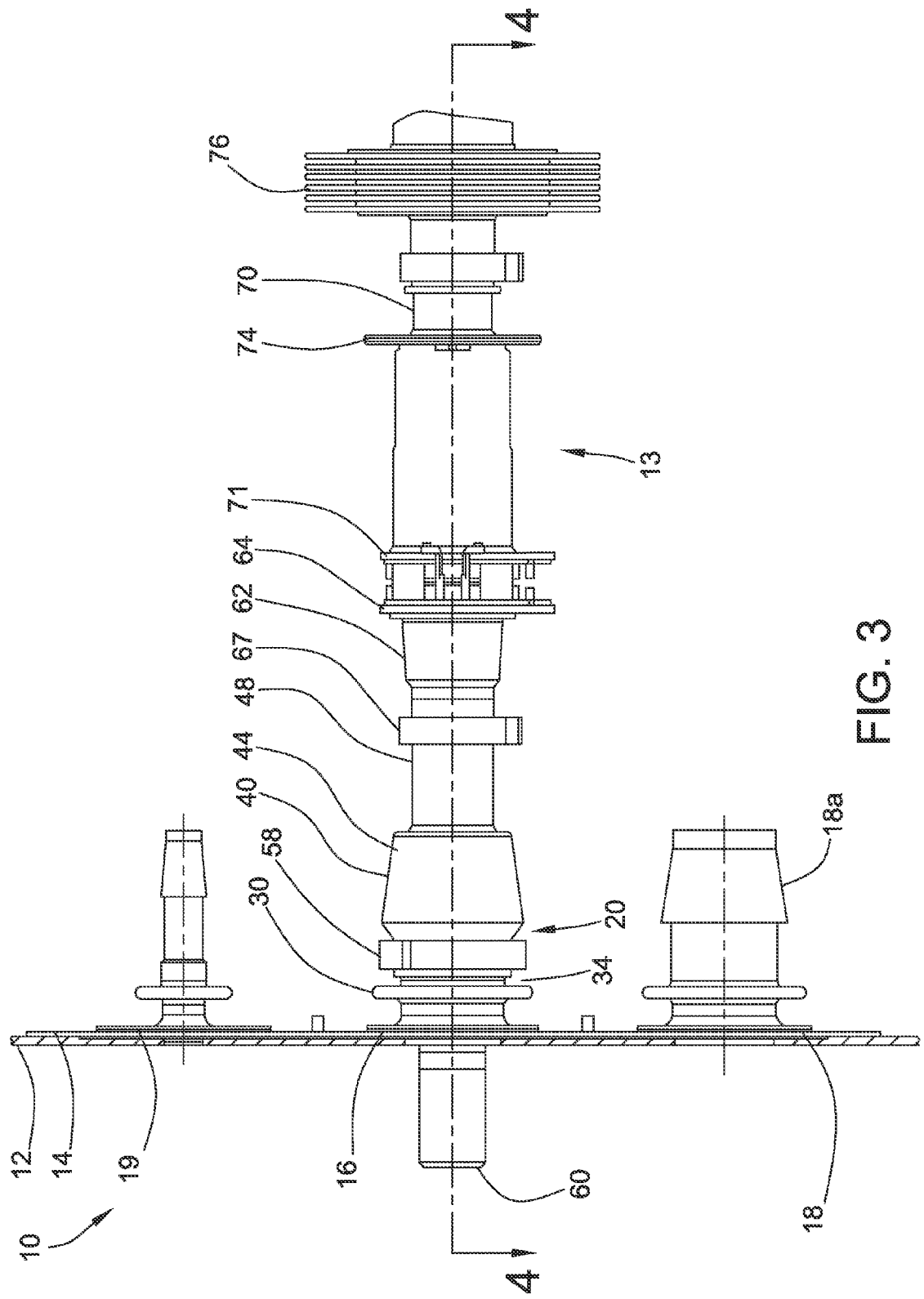
FIG. 3 is an enlarged front view of a processing chamber having a fully assembled sensor port manifold, a sensor probe seal and a portion of a sensor assembly.
Figure 4:
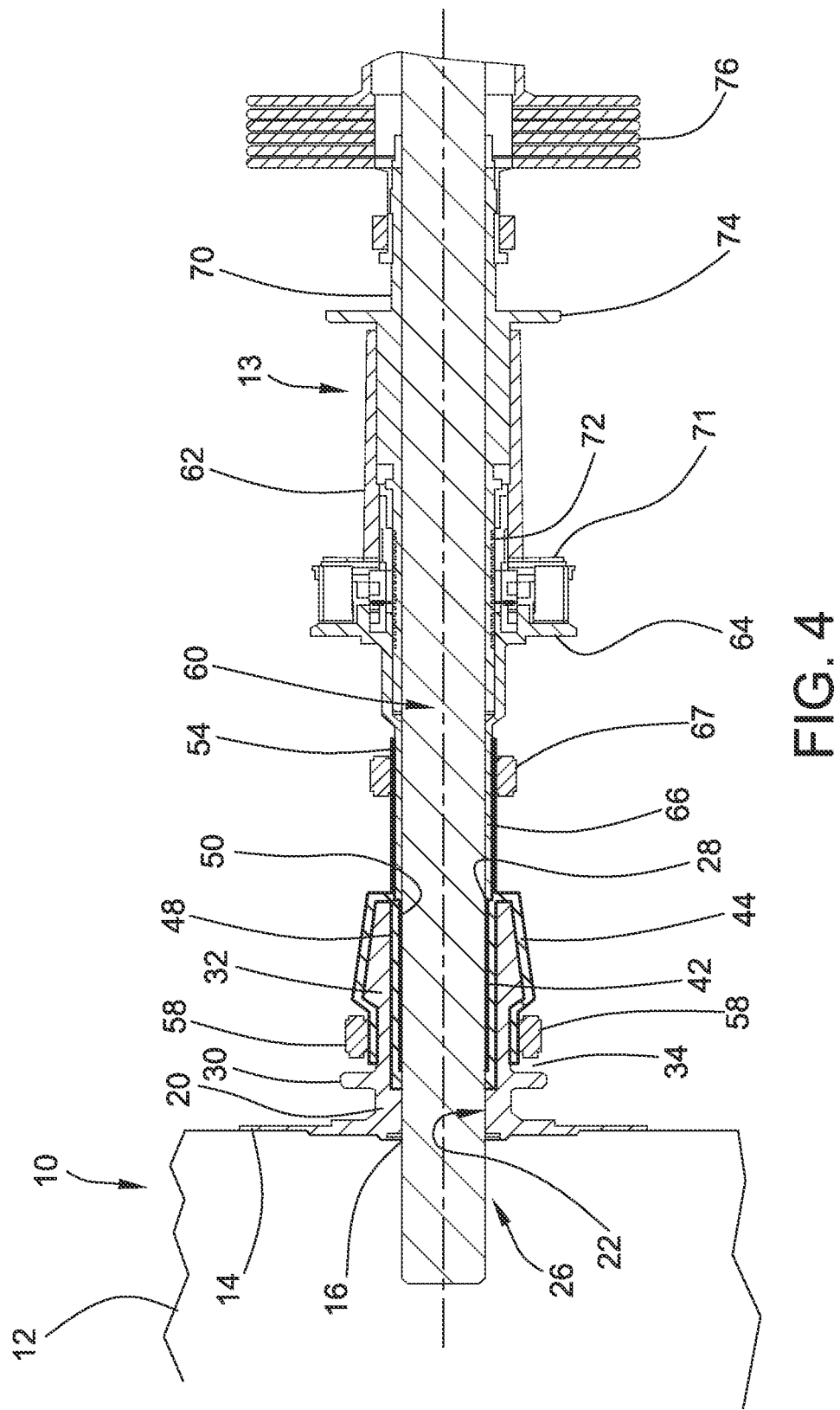
FIG. 4 is a cross-sectional view of a processing chamber having a fully assembled sensor port manifold, a sensor probe seal and a portion of a sensor assembly taken along line 4-4 in FIG. 3.

FIGS. 1-4 illustrate one embodiment of a sensor assembly 13 for measuring conditions such as temperature, pH, and the like within the processing chamber 12. FIG. 1 illustrates the female unit 62 of the sensor probe assembly 13 without a sensor probe 60. FIGS. 3-4 illustrate the female unit 62 and male unit 70 of the sensor assembly 13. In the illustrated embodiment, the female unit 62 is typically attached to the processing chamber 12 while the chamber 12 is empty and before the fluid fills the chamber 12. A sensor probe 60, which is generally attached to the male unit 70, is connected to a data recorder and/or a control unit (not shown) for measuring the conditions in the chamber 12. When the male and female units are attached to each other, the sensor probe 60 may be inserted into the processing chamber 12.

FIGS. 1-4 show a sensor manifold 14 disposed on the exterior of the processing chamber 12. The sensor manifold 14 has at least one port 16 for receiving and permitting a sensor probe 60 to access the interior of the processing chamber 12. The illustrated sensor manifold 14 has three spaced-apart ports 16, 18, 19. In a preferred embodiment, the ports 16, 18 are adapted to receive sensor probes 60 and port 19 is a fluid sampling port. Port 18 is not in use and has a cover 18a. Sensor port 16 comprises a stem 20 projecting outwardly from the manifold 14. The stem 20 comprises an interior wall 22 forming a stem passageway 24 disposed between inner and outer openings 26, 28, respectively. The stem 20 also comprises an annular flange 30 and a tapered flange 32. A channel 34 is formed between the two flanges 30, 32.

In accordance with the present invention, a probe seal 40 is provided that forms a reliable seal between the sensor port 16 and the sensor probe 60 which prevents fluid in the processing chamber 12 from leaking past the probe seal 40. Without the probe seal 40, it will be appreciated that fluid in the processing chamber 12 may enter and accumulate in the stem passageway 24 and the sleeve surrounding the sensor probe 60. If the sensor assembly 13 is disassembled or the sensor probe is withdrawn without the probe seal 40, any accumulated fluid may leak out of the manifold and/or probe assembly. The fluid product contained within the probe sleeve may also become unviable.

The probe seal 40, which forms a liquid-tight seal between the stem 16 and the sensor probe 60, comprises inner and outer skirts 42, 44, respectively. The inner and outer skirts 42, 44 are preferably formed of an integrally formed flexible material such as molded silicone. A seal passageway 46 formed by the inner skirt 42 permits the sensor probe 60 to pass through the probe seal 40 and the stem passageway 24 and enter the processing chamber 12. By selecting pre-determined dimensions for the inner skirt 42, preferably based on o-ring design dimensions, the flexible inner skirt 42 compresses against the probe sensor 60 and the stem passageway 24 effecting a leak-tight seal between the stem 20 and probe sensor 60.

The inner skirt 42 has outer wall 48, inner wall 50, and a seal member 52. The outer wall 48 engages the interior wall 22 of the stem passageway 24. The inner wall 50 forms a seal passageway 46 which is adapted to receive the sensor probe 60. An outer end 54 of the inner skirt 42 enables the probe seal 40 to be releasably attached to female unit 62 of the probe assembly using a cable tie 67 or the like. The sensor probe 60 may be inserted through the seal passageway 46 and then port passageway 24 so it may measure the fluid in the processing chamber 12.

Figure 5:
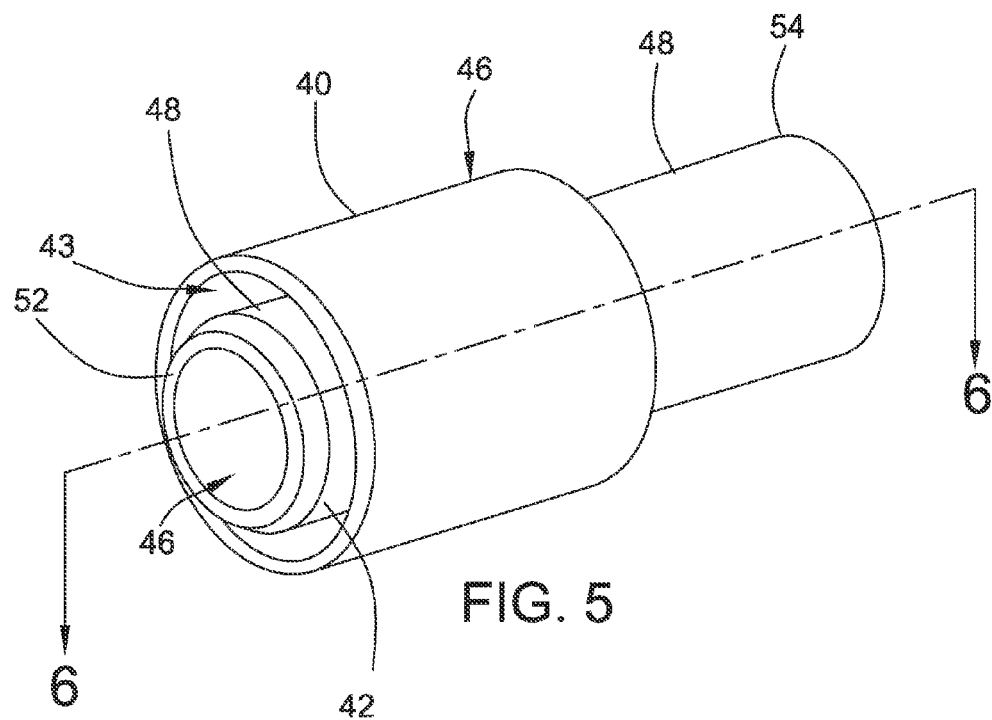
FIG. 5 is a perspective view of a probe seal.
Figure 6:
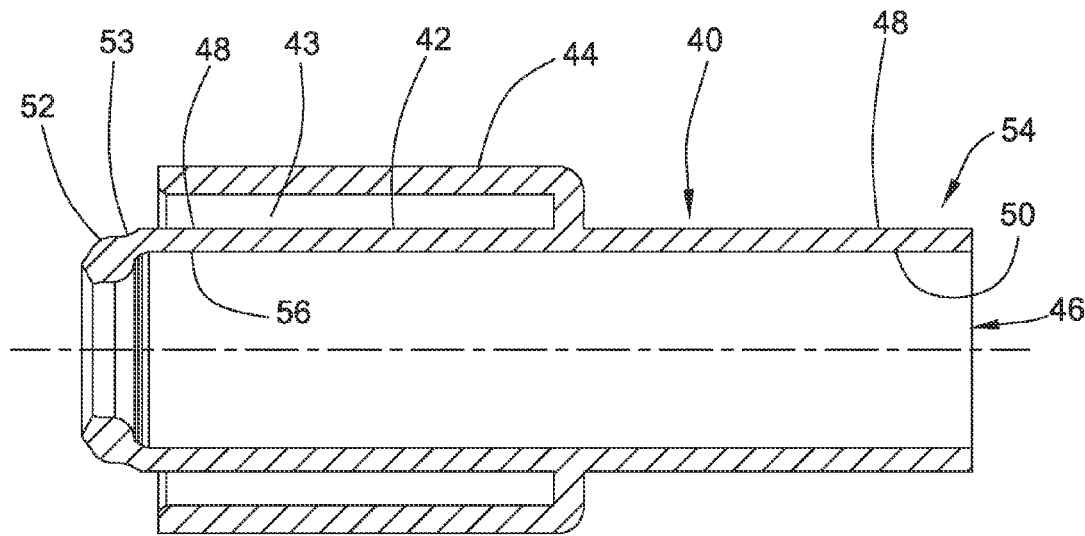
FIG. 6 is a cross sectional view of the probe seal taken along line 6-6 in FIG. 5.

The seal member 52 is located near the inner end 56 of the inner skirt 42 which is inserted into the stem passageway 24. A neck 53 between the seal member 52 and the inner skirt 42 permits the seal member 52 to taper and/or curve inwardly towards the centerline of the probe seal 40 and away from the wall 22 forming the stem passageway 24. As best shown in FIGS. 5-6, the seal member 52 extends outboard of the outer skirt 44. Disposing the seal member 52 outboard of the outer skirt 44 and inwardly tapering the seal member 52 facilitates insertion of the inner skirt 42 into the stem passageway 24 during assembly, and also minimizes damage to the seal member 52 and the inner skirt 42 by the stem passageway 24. When the sensor probe 60 is inserted through the probe seal 40 into the processing chamber 12, the sensor probe 16 pushes the seal member 52 outwardly towards the wall 22 of the passageway 24. A compressible liquid-tight seal between the sensor probe 60 and the wall 22 of the stem passageway 24 is formed in response to the movement of the sensor probe 60.

In a preferred embodiment best shown in FIG. 6, the seal member 52 has a generally circular or oval configuration. To effectuate a seal between the sensor probe 60 and stem wall 22, the thickness of the seal member 52 is preferably larger than the thickness of the inner skirt wall. Thus, in response to insertion of the sensor probe 60 through the probe seal passageway 24, the seal member 52 sealably engages the sensor probe 60 without interference from wall 50 of the inner skirt 48. To facilitate flexing of the seal member 52 in response to the sensor probe 60, it is also preferable that the thickness of the neck 53 is smaller than the skirt thickness.

The outer skirt 44 is spaced apart from the inner skirt 42 so a skirt channel 43 is formed between the inner and outer skirts 42, 44. The skirt channel 43 is adapted to receive the tapered flange 32 of the stem 20 when the inner skirt 42 is pushed into the stem passageway 24. The flexible polymeric material permits the outer skirt 44 to flex and accommodate the tapered flange 32. The probe seal 40 may be releasably attached to the stem 20 using a cable tie 58 and the like. The cable tie 58 also acts to prevent fluid in the processing chamber 12 from leaking outside between the probe seal 40 and stem flange 32.

To use the present invention, a probe seal 40 is releasably attached to the stem 20 by inserting the inner end 56 of the probe seal 40 into the stem passageway 24. The seal member 52, which is disposed outboard of the outer skirt 44 and tapers inwardly toward the center of the probe seal, facilitates insertion of the inner skirt 42 into the stem passageway 24 during assembly, and also minimizes damage to the seal member 52 and the inner skirt 42 by the stem passageway 24. The outer wall 48 of the inner skirt 42 slidably engages the interior wall 22 of the stem passageway 24. The inner wall 50 forms a seal passageway 46 which is adapted to receive the sensor probe 60.

When the inner skirt 42 is inserted into the stem passageway, the skirt channel 43 formed between the inner and outer skirts 42, 44 receives the tapered flange 32 of the stem 20. The flexible polymeric material permits the outer skirt 44 to flex and accommodate the tapered flange 32. A cable tie 58 which is adapted to fit within the channel 34 may be used to releasably attach the outer skirt 44, and thus the probe seal 40, to stem 20.

Once the probe seal 40 is attached to the stem 20, the female unit 62 of the sensor assembly 13 may be inserted into the outer end 54 of the inner skirt 42. A cable tie 67 may be used to releasably attach the female unit 62 to the probe seal 40. Using the flange 74, the male end 70 of the sensor assembly 13 may be inserted into the female end 62. The female end 62 and male end 70 may be releasably attached to each other using the female and male latching members 64, 71, respectively.

After the male and female units 62, 70 are attached to each other, the sensor probe 40, which is initially housed in a sleeve 76, may be inserted through the seal passageway and the stem passageway and into the chamber 12. The sensor probe 40 is ejected from the interior of the sleeve 76 by pushing and collapsing the sleeve as shown in FIG. 3.

Prior to insertion of the probe seal 40 into the seal passageway 46, the seal member 52 tapers and/or curve inwardly towards the centerline of the probe seal 40 and away from the wall 22 forming the stem passageway 24. When the sensor probe 60 is inserted through the probe seal 40 into the processing chamber 12, the sensor probe 16 engages the seal member 52 and pushes the seal member 52 outwardly towards the wall 22 of the passageway 24. A compressible liquid-tight seal between the sensor probe 60 and the wall 22 of the stem passageway 24 is formed in response to the movement of the sensor probe 60. To facilitate a seal between the sensor probe 60 and stem wall 22, the thickness of the seal member 52 is preferably larger than the thickness of the inner skirt wall. Thus, in response to insertion of the sensor probe 60 through the probe seal passageway 24, the seal member 52 sealably engages the sensor probe 60 without interference from wall 50 of the inner skirt 48.

It will be appreciated that fluid in the processing chamber 12 may enter and accumulate in the stem passageway 24 and the sleeve surrounding the sensor probe 60 if the probe seal 40 was not present. Similarly, if the sensor assembly 13 is disassembled or the sensor probe is withdrawn without the probe seal 40, any accumulated fluid may leak out of the manifold and/or probe assembly and/or the fluid in the probe sleeve may also become unviable. Thus, in accordance with the present invention, a probe seal 40 is provided that forms a reliable seal between the sensor port 16 and the sensor probe 40 to prevent fluid in the processing chamber from leaking past the probe seal 40.

This disclosure is intended to be illustrative and not exhaustive. The disclosure will suggest many variations and alternatives to one of ordinary skill in the art. All these variations and alternatives are intended to be included within the scope of the present invention and appended claims. Those familiar with the art may recognized other equivalents to the embodiments described herein which are intended to be included within the scope of the present invention and appended claims.

We claim:

1. A biological processing system comprising:
   a chamber having an interior for receiving and processing fluids;
   a sensor assembly having a sensor probe for measuring conditions in the chamber;
   at least one port disposed on the chamber for receiving the sensor probe and permitting the sensor probe to access the chamber interior, wherein the port comprises a stem projecting outwardly from the chamber, and the stem comprises a tapered flange and an interior wall forming a stem passageway disposed between interior and outer openings and in fluid communication with the chamber interior;
   a probe seal for forming a seal between the port and the sensor probe and preventing fluid in the chamber from leaking past the probe seal, wherein the probe seal comprises spaced-apart inner and outer skirts, the inner skirt having a wall forming a seal passageway for receiving the sensor probe and permitting the sensor probe to enter the chamber interior when the probe seal is attached to the stem;

wherein the inner skirt has a seal member for sealably compressing against the probe sensor and the stem passageway to form a leak-tight seal; and wherein the inner and outer skirt form a skirt channel adapted to receive the tapered flange of the stem when the inner skirt is inserted into the stem passageway.

2. The system set forth in claim 1 wherein the flange of the stem has a tapered configuration and the stem further comprises an annular flange disposed between the chamber and the tapered flange, and wherein a stem channel is defined between the annular and tapered flanges;

a cable tie for releasably attaching the probe seal and stem together; and wherein the probe seal is comprised of a flexible polymeric material adapted to permit the outer skirt to flexibly engage the tapered flange when the inner skirt is inserted into the stem passageway, and the outer skirt is disposed to be attached to the stem channel with the cable tie.

3. The system set forth in claim 1 wherein the seal member is located near the interior end of the inner skirt which is inserted into the stem passageway and tapers inwardly towards the probe sensor and away from the wall forming the stem passageway.

4. The system set forth in claim 3 wherein the inner skirt comprises a neck disposed between the seal member and the inner skirt, and the neck is thinner than the wall of the inner skirt so that the neck permits the seal member to flex outwardly into sealing engagement with stem passageway in response to insertion of the probe seal into the seal passageway.

5. The system set forth in claim 3 wherein the seal member is disposed outboard of the outer skirt to facilitate insertion of the inner skirt into the stem passageway.

6. The system set forth in claim 1 wherein the seal member is thicker than the inner skirt wall so that when the sensor probe is inserted through the probe seal passageway, the seal member may sealably engage the sensor probe without interference from wall of the inner skirt.

7. A sealing system for preventing leakage of a fluid from a fluid-containing chamber when a sensor probe for measuring fluid conditions within the chamber is inserted into the chamber, the sealing system comprising:

at least one port in fluid communication with the fluid-containing chamber, wherein the port comprises a stem projecting outwardly from the chamber, and the stem comprises a tapered flange and an interior wall forming a stem passageway disposed between interior and outer openings and in fluid communication with the chamber interior;

a probe seal for forming a seal between the port and the sensor probe and preventing fluid in the processing chamber from leaking past the probe seal, wherein the probe seal comprises spaced-apart inner and outer skirts, and wherein the inner skirt comprises a wall forming a seal passageway wherein the seal passageway is in fluid communication with the chamber, and wherein the inner skirt comprises an interior end disposed to enter the stem passageway when the probe seal is attached to the stem; and wherein the inner skirt has a seal member disposed near the interior end for sealably compressing against the probe sensor and the stem passageway to form a leak-tight seal in response to insertion of the sensor probe into the seal passageway; and wherein the inner and outer skirt form a skirt channel adapted to receive the tapered flange of the stem when the inner skirt is inserted into the stem passageway.

8. The system set forth in claim 7 wherein the flange of the stem has a tapered configuration and the stem further comprises an annular flange disposed between the chamber and the tapered flange so that the a stem channel defined between the annular and tapered flanges;

a cable tie for releasably attaching the probe seal and stem together; and wherein the probe seal is comprised of a flexible polymeric material adapted to permit the outer skirt to flexibly engage the tapered flange when the tapered flange is inserted into the skirt channel, and the outer skirt is disposed to be attached to the stem channel with the cable tie.

9. The system set forth in claim 7 wherein the seal member is located near the interior end of the inner skirt which is inserted into the stem passageway and tapers inwardly towards the probe sensor and away from the wall forming the stem passageway.

10. The system set forth in claim 9 wherein the inner skirt comprises a neck disposed between the seal member and the inner skirt, and the neck is thinner than the seal member so that the neck permits the seal member to flex outwardly into sealing engagement with stem passageway in response to insertion of the probe seal into the seal passageway.

11. The system set forth in claim 9 wherein the seal member is disposed outboard of the outer skirt to assist insertion of the inner skirt into the stem passageway.

12. The system set forth in claim 7 wherein the seal member is thicker than the inner skirt wall so that when the sensor probe is inserted through the probe seal passageway, the seal member may sealably engage the sensor probe without interference from wall of the inner skirt.

* * * * *